United States Patent [19]

Chaudhry et al.

[11] Patent Number: 6,096,330
[45] Date of Patent: Aug. 1, 2000

[54] ALKYLPHOSPHINES AS PESTICIDAL AGENTS

[75] Inventors: Mohammad Oasim Chaudhry; Alan Donald Macnicoll; Nicholas Raymond Price, all of Sand Hutton, United Kingdom

[73] Assignee: The Secretary of State for Minister of Agriculture Fisheries & Food in Her Britannic Majesty's Government of the United Kingdom of Great Britain and Northern Ireland, London, United Kingdom

[21] Appl. No.: 09/077,247

[22] PCT Filed: Nov. 21, 1996

[86] PCT No.: PCT/GB96/02876

§ 371 Date: May 19, 1998

§ 102(e) Date: May 19, 1998

[87] PCT Pub. No.: WO97/18714

PCT Pub. Date: May 29, 1997

[30] Foreign Application Priority Data

Nov. 22, 1995 [GB] United Kingdom .................. 9523832
Jul. 5, 1996 [GB] United Kingdom .................. 9614164

[51] Int. Cl.[7] ............................ A01N 25/00; A01N 57/18
[52] U.S. Cl. ............................ 424/405; 424/45; 424/406; 514/134; 514/135
[58] Field of Search ..................................... 424/405, 406, 424/45; 514/134, 135

[56] References Cited

U.S. PATENT DOCUMENTS 3,054,718  9/1962  Gordon et al. ............................ 167/22

FOREIGN PATENT DOCUMENTS

| 0132881 | 2/1985 | European Pat. Off. . |
| 1431162 | 5/1966 | France . |
| 3436380 | 4/1986 | Germany . |
| 62-277309 | 5/1986 | Japan . |
| 871190 | 6/1961 | United Kingdom . |
| 2141123 | 12/1984 | United Kingdom . |
| 2177004 | 1/1987 | United Kingdom . |

OTHER PUBLICATIONS

Chaudry et al, 1996, Phytoparasitica, 24:216.
Crosbie et al, 1969, J. Inorg Nucl Chem, 31:3684–5.
Rajendran, 1990, Pesticide Science, 29:75–83.
Roland et al, 1986, Chem Ber, 119:2566–81.

*Primary Examiner*—Neil S. Levy
*Attorney, Agent, or Firm*—Klauber & Jackson

[57] ABSTRACT

A method for controlling pests comprising administering to them a compound of the formula (i) R-PH-R', wherein R is a $C_1$–$C_6$ aliphatic hydrocarbyl group and R' is H or a $C_1$–$C_6$ aliphatic hydrocarbyl group. Either hydrocarbyl group may be optionally substituted. Preferably, the compound of formula (i) is metliylphosphiine. The method has particular utility against insects which are resistant to phosphine. Also disclosed are pesticidal compositions of compounds of formula (i), and methods and compositions combining these compounds with phosphine.

12 Claims, No Drawings

ALKYLPHOSPHINES AS PESTICIDAL AGENTS

This application was filed under 35 U.S.C. §371 and is based on international application number PCT/GB96/02876, citing priority of Great Britain applications numbers 9523832.5 and 9614164.3.

The present invention relates to methods and compositions having a pesticidal effect. The invention further relates to methods of preparation and use of pesticidal agents and compositions.

There is an ongoing requirement for materials having pesticidal activity e.g. for use in post-harvest protection of foodstuffs, the sterilisation of soil, or in insect-mediated disease control. In particular, novel materials are required to overcome the problem of resistance to existing agents.

Phosphine gas ($PH_3$) has been extensively used for the past four decades to control insect pests of food-grains and other stored commodities. $PH_3$ fumigation does not leave toxic residues in the food, and the availability of solid phosphide formulations that generate the gas in situ have made PH3 a Fumigant of choice throughout the world. In fact, with the recent restrictions on production of the other alternative, methyl bromide ($CH_6Br$), due to possible deleterious effects on the environment, $PH_3$ is becoming the only fumigant available for disinfecting stored food commodities. The future availability of $PH_3$ as a fumigant is especially important for developing countries where grain storage is mainly in bags and the technology for the application of non-gaseous grain protectants is not available.

The emergence of $PH_3$ resistance in several species of stored-product insects in the past two decades has however threatened the use of this fumigant. $PH_3$ resistance has now been reported from many countries and is linked to poor fumigation practices leading to selection of resistant insect strains. It is particularly alarming that in some instances resistance has reached a level where it can lead to control failures even when the best current fumigation practices are applied.

In view of the importance of $PH_3$ in post-harvest management of grains and other commodities, its mode of action, and the mechanism of resistance to $PH_3$ in insects, have been the subject or a number of studies.

Regarding mode of action, the metabolism of $PH_3$ in insects has been suggested to be oxidative, ultimately resulting in essentially non-toxic oxyacids of phosphorus mainly hypophosphite, phosphite and orthophosphate. The process possibly involves formation of unstable intermediate phosphine oxide [$H_3P(O)$] and leads to the disruption of normal $O_2$-metabolism. and generation of highly deleterious oxyradicals in insects (see e.g. Chaudhry & Price (1992) Pestic Biochem Physiol 42: 167–179).

Regarding resistant insects, the use of 32P-radiolabelled $PH_3$ revealed that resistant insects absorb very small amounts of the gas compared to their susceptible counterparts. The resistant strains of several species of stored-product insects, some collected from different countries, were found to exhibit the same phenomenon (see e.g. Chaudhry & Price (1989) Comp Biochem Physiol 94C(2): 425–429; Chaudhry & Price (1990) J stored Prod Res 26(2): 101–107) indicating a common mechanism of $PH_3$-resistance in insects. The amount of $PH_3$ absorbed by some live resistant insects was even lower than that passively absorbed by dead insects and an active exclusion of $PH_3$ in resistant insects was proposed (Price (1984) J stored Prod Res 20(3): 163–168). This phenomenon was also confirmed by pulse-chase studies where a higher respiratory exclusion of the gas was found in the resistant insects than in the susceptible ones (Chaudhry & Price, 1992, supra). Other studies have indicated that the reduced uptake of $PH_3$ was not the only underlying mechanism of resistance and the involvement of an additional detoxification process was established (Chaudhry & Price, 1990, supra). This was supported by conventional genetic studies that at least two genes were linked to $PH_3$-resistance in insects (Ansell et al, Proc 5th Working Conference on Stored Product Protection, Bordeaux, 1990, 961–970).

One common approach to the problem of controlling resistant insects has been to try and increase the efficacy of $PH_3$ application by improving fumigation practices. This includes improving the gastightness of the space to be fumigated (Banks & Ripp (1984) Proc 3rd Int Working Conf on Stored Product Entomology, pp 375–388, Kansas State University, Manhattan, Kans., USA). Also the use of formulations which release $PH_3$ at a slower rate (Halliday (1986) Proc. "GASGA Seminar on Fumigation Technology in Developing Countries", pp. 19–23, TRDI, London), application of multiple doses (Friendship et al (1986) Proc "GASGA Seminar on Fumigation Technology in Developing Countries", pp 141–149, TDRI, London) and maintaining a low level of PH3 by its continuous supply from cylinder with the help of a pump (Anderson (1989) New Scientist, 122:38). A 14% level of $CO_2$ has been reported to increase the respiratory activity and thus enhance the uptake and efficacy of PH3 in insects (Kashi & Bond (1975) J stored Prod Res 11: 9–15). A mixture of $PH_3$ in $CO_2$ has therefore been used to increase the efficacy of phosphine against insects (Desmarchelier et al (1984) Proceedings of an international symposium 'Practical aspects of controlled atmosphere and fumigation in grain storages', pp 75–81, held from 11 to 22 April, 1983 in Perth, Western Australia ; El-Lakwah et al (1991) Zeitschrift fur Pflanzenkrankheiten und Pflanzenschutz, 98(1): 92–102; Muller (1994) Pest Control, 62(3): 42–48.

However, none of the methods available to date can be satisfactorily used to effectively and selectively control $PH_3$-resistant insects.

Another approach to the problem of $PH_3$-resistant insects is to move away from the use of $PH_3$ altogether. Thus one PCT Application (Publication No. WO 93/13659; Banks et al.) discloses the use of carbonyl sulphide (COS) gas as a fumigant. The insecticidal action of COS is suggested to arise from the hydrolysis of carbonic annydrase to produce $H_2S$ and $CO_2$ inside the insects.

However, the high aqueous solubility of COS, and breakdown of the solubilised gas to $H_2S$, which might lead to sulphurous residues in the fumigated commodities, means that it may not be a safe alternative to $PH_3$.

Another commonly used agent, in this case generally used as a volatile liquid for the treatment of commodities and sterilisation of soil, is $CH_3Br$. However, as described above, the future availability Of $CH_3Br$ has recently become doubtful because of its ozone-depleting effects on the environment.

In the light of these factors, the present inventors set out to make available a new fumigating agent which could substitute for the use of one or more of the presently used agents (such as $PH_3$ and $CH_3Br$) and in preferred forms could also be used to specifically control $PH_3$-resistant insects.

The present inventors have now demonstrated that a lower-alkyl phosphine (methylphosphine; $CH_3PH_2$) is a potent fumigant, and also has much higher toxic effects on $PH_3$-resistant insects than their susceptible counterparts.

This is the first time that such properties have been demonstrated in a substituted phosphine.

Thus in a first aspect of the invention there is disclosed a method for controlling pests comprising administering a compound of the formula (i) to them:

   formula (i):

wherein R is a $C_1$–$C_6$ aliphatic optionally substituted hydrocarbyl group and R' is H or a $C_1$–$C_6$ aliphatic optionally substituted hydrocarbyl group.

Preferably R' is H and R is $C_1$–$C_4$ aliphatic optionally substituted hydrocarbyl group. Preferably the compound is an alkylphosphine, and most preferably a lower-alkylphosphine.

By optionally substituted is meant that the hydrocarbyl group may be substituted by one or more groups selected from oxo, mercapto, halo, such as fluoro, chloro, bromo or iodo, nitro, cyano, amino, amido, or hydroxy provided that such substitution is such that the compound still has pesticidal activity and thus has utility in the methods of the present invention. This may be readily ascertained by the skilled person, in the light of the present disclosure, by employing the methods of the examples set forth below.

Preferably the compound is used in sufficient dosage that the pests are killed by the administration.

Preferably the pests are insects, mites, nematodes, fungi and bacteria; the invention is particularly advantageous when used. against those pests which have traditionally been treated by $PH_3$, such as are referred to in numerous prior art papers e.g. those above. The invention has particular utility in treating insects which have become resistant to $PH_3$ i.e. insects which can survive doses of $PH_3$ designed to discriminate between susceptible and resistant con-specifics.

The administration can take any form which brings the pests into contact with the compound of formula (i) i.e. the agent does not have to be administered directly to isolated insects, but may be administered to items (e.g. grain) suspected of being contaminated with them. Other possible items include dried fruit, coffee, tobacco, timber, cut flowers, quarantine material and also foodstuff containers, ships, grain stores, silos, greenhouses etc.

The compound of formula (i) may include branched or unbranched aliphatic hydrocarbyl groups. In one form the agent is gaseous at the ambient temperature at which it is employed, which will generally speaking be 'room temperature' and is employed as a gaseous fumigant. Methylphosphine may be particularly advantageous to this end.

If the agent is to be used for the sterilisation of soil or other non-consumable solid materials then it may be desirable that it is in the form which is a volatile liquid at the ambient temperature at which it is used. In this regard the agent provides an alternative to the commonly used $CH_3Br$ rather than phosphine and mono-substituted or di-substituted phosphines employing heavier, optionally substituted, alkyl groups such as ethyl-, propyl- or butyl-, may be particularly advantageous. The target pests in this case are not only insects, but also nematodes, bacteria, fungi etc.

In one, preferred, embodiment of the first aspect the compound of formula (i) is administered in conjunction with PH3. Conjunction as used herein means that the two are used together in such a way that the effect of one complements the effect of the other e.g. simultaneously, or one following the other. Such a combination has the advantage that it can be used efficiently with both resistant- and non-resistant pests, which are targeted by the compound of formula (i) and the $PH_3$ respectively.

It may be desirable to alternate the use of the compound of formula (i) and PH3 in order to prevent build up of resistance to either.

In a second aspect of the invention there are disclosed compositions having utility in the methods of the first aspect.

Thus compositions comprising gaseous or liquid compounds of formula (i), such as are discussed above, plus carrier gasses (e.g. $N_2$) or $CO_2$. Preferably the compound of formula (i) constitutes at least 1%, more preferably at least 5, 10, or 50% and most preferably at least 85% of the composition, with the remainder being carrier gas or $CO_2$. Higher concentrations may reduce transport costs and will increase effectiveness. However, in practice, and depending on transporting and dispersing requirements, it may be desirable to have the compounds of formula (i) at a concentration selected to. minimise flammability, or other handling hazards. For instance at a concentration of less than 5, 4, ,3 or 2% with the remainder being a non-flammable, or flame supporting, carrier gas or $CO_2$.

Essentially these compounds of formula (i), and in particular gaseous alklyphosphines, may be used in analogous compositions to those by which $PH_3$ is presently employed, and such as are familiar to those skilled in the art.

In one, preferred, embodiment of the second aspect there is disclosed a composition comprising a compound of formula (i) and $PH_3$. Such a composition may be used efficiently with both resistant- and non-resistant pests. Preferably the compound of formula (i):$PH_3$ ratio is around 2:1. More preferably the compound of formula (i): $PH_3$ ratio is selected such that the composition has approximately equivalent pesticidal affect against phosphine resistant and phosphine susceptible pests.

Thus the invention makes available compositions and methods which can be used advantageously in the control of pests in general, and $PH_3$-resistant insects in particular.

Earlier work done by the inventors suggests a possible explanation for the novel and unexpected efficacy demonstrated by methylphosphine as a fumigant, particularly in relation to $PH_3$-resistant insects Work was carried out using arsine ($AsH_3$) and stibine ($SbH_3$) the trihydrate gases of group Vb elements that are analogous to $PH_3$. A comparison of the toxic effects in the susceptible and $PH_3$-resistant insects showed a negative correlation between insect resistance to $PH_3$ and their tolerance to both arsine and stibine (Chaudhry a Price (1991) Comp Biochem Physiol 99C: 41–45). This indicated that, unlike $PH_3$, the active exclusion mechanism probably failed to exclude arsine and stibine whilst the detoxification process produced toxic metabolites, arsenite and antimonite, causing a higher mortality in the $PH_3$-resistant insects (Chaudhry & Price, 1991, supra).

Unfortunately, arsine and stibine both produce toxic residues and this reduces their desirability for use as a fumigant. Two silicone hydride gases were similarly tested but their biological efficacy was not comparable to the hydride gases of group Vb elements i.e. $PH_3$, arsine and Stibine.

However the studies, in the light of the present invention, suggest that agents which mimic $PH_3$ but have a different chemical structure may be able to avoid the mechanism of active exclusion in the resistant insects. Additionally, having a different chemical structure, the agents may be able to interfere with the detoxification mechanism used for $PH_3$, and if the metabolites resulting from these agents were not non-toxic (as in the case of $PH_3$) then it would be possible to selectively kill the $PH_3$-resistant insects.

Thus in a further aspect of the invention there is disclosed a method for selectively killing pesticide-resistant pests in favour of pesticide-susceptible pests wherein the resistant pests employ a metabolic pathway not found in the susceptible pests which is capable of metabolising the pesticide to a non-toxic metabolite comprising administering an agent to said pests which is metabolised by the metabolic pathway to a toxic metabolite.

The presence of the distinguishing metabolic pathway may be inferred by those skilled in the art e.g. by experiments such as those outlined above.

By careful use of an agent (e.g. methylphosphine) to selectively kill pesticide-resistant pests, it should be possible to prolong the useful life of the pesticide (e.g. $PH_3$) which would otherwise ultimately become redundant owing to widespread resistance in the target population.

The methods, agents and compositions of the present invention will now be described, by way of illustration only, through reference to the following non-limiting examples. Other embodiments falling within the scope of the invention will occur to those skilled in the art in the light of these.

EXAMPLES

Example 1—General Methodology

INSECT SPECIES, STRAINS AND CULTURE: Four species so stored-product insects used in the toxicity tests were the lesser grain borer (Rhyzopertha dominica); the rust-red flour beetle (Tribolium castaneum); the rice weevil (Sitophilus oryzae); and the flat grain beetle (Cryptolestes ferrugineus).

Three strains of R dominica used in the tests were a susceptible (reference), a laboratory selected $PH_3$-resistant (306-sel) and a highly resistant field strain (BR2) which originated in Bangladesh. The T castaneum strains tested were a susceptible (lab) and a PH3-resistant strain collected from Bangladesh (BT-1vs). The strains of S oryzae included a susceptible (reference) and a $PH_3$-resistant (476) strain whereas C ferruginous strains included a susceptible (reference) and a resistant (BC12s) strain. In all the tests, 4–8 week old adult insects were used.

All insect strains were cultured at 25° C. at 70% R.H. R dominica and S oryzae were reared on whole wheat, T castaneum on wheat flour containing 5% yeast and C ferruginous on wheat flakes.

PREPARATION OF METMYMPHOSPHINE: Methylphosphine was prepared by reaction of dimethyl-methylphosphonate and lithium-allrninium-hydride ($LiAlH_4$) in ethylene glycol dimethyl ether (monoglyme) under nitrogen atmosphere in a slight modification to the method described by Crosbie and Sheldrick (1969) J Inorg Nucl Chem 31: 3684–3685.

In a first method ('Method 1'), Dimethyl-methylphosphonate (160 mg) was placed in a gastight reaction tube (100 ml volume) fitted with rubber'septum and kept under the flow of dry nitrogen gas for 30 minutes. The tube was cooled on dry-ice to control the vigorous reaction before adding a stoichiometric amount of lithium aluminium hydride (0.5M in monoglyme). Both reagents were mixed while cold and the flow of nitrogen gas was stopped by sealing the reaction tube. The reactants were brought to room temperature and allowed to react for 30 minutes before any sample of methylphosphine was drawn though the rubber septum using a gastight syringe.

The yield of methylphosphine gas by Method 1 was assumed to be 87% (Crosbie & Sheldrick (1969) supra).

A second, alternative, method ('Method 2') was as follows. In a typical synthesis, a pellet of $LiAlH_4$ weighing about 2.5 g (Aldrich Chemical Co., U.K.) was added to 15 ml of monoglyme in a three-neck flask fitted with a rubber septum and maintained under a flow of nitrogen gas. The hydrogen gas produced due to reaction of the $LiAlH_4$ with any traces of moisture was discarded through a bubbler containing 2% mercuric chloride ($HgCl_2$) solution whilst the pellet was stirred in monoglyme to form a slurry. About 1.60 g of dimethyl-methylphosphonate (Aldrich Chemical Co., U.K.) were added very slowly into the slurry with stirring. Methylphosphine generated in the reaction was collected in a stream of nitrogen gas over the surface of water in a glass burette fitted with a rubber septum. The identity of methylphosphine was confirmed by mass spectromnetric analysis, which was consistent with the previously reported mass spectrum of methylphosphine Wada & Kiser (1964) J Physic Chemistry 68(8):2290–2295.

The concentration of methylphosphine was measured by Gas Chromatogaphy (GC) using a Shimadzu-GC-9A, fitted with a glass-lined packed column (1 m long, ⅛" O.D., Poropak-QS 80–100 packing), flame photometric detector and automatic gas sampling gas sampling loop. The column temperature was maintained at 200° C., with injector and detector temperatures at 150° C. Methylphosphine was eluted from the column immediately after PH3 (retention times 0.255 and 0.397 minutes respectively for $PH_3$ and methylphosphine), and the amounts estimated by comparison to standard concentrations of $PH_3$. A correction factor was used to account for the difference in molecular weights of $PH_3$ and methylphosphine.

In some cases, concentrations of methylphosphine measured by GC were verified by chemical analysis. This was carried out by reacting a known volume of methylphosphine with standard $HgCl_2$ solution and titrating the amount of HCl produced in the following reaction, with NaOH solution:

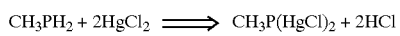

$$CH_3PH_2 + 2HgCl_2 \Longrightarrow CH_3P(HgCl)_2 + 2HCl$$

Example 2—Effect of Methylphosphine Alone and in Combination with Phosphine on Resistant and Susceptible Insects ADMINISTRATION OF METHYLPHOSPHINE TO INSECTS: Treatment of insects with methylphosphine gas was carried out in gastight desiccators of 6.25 litres volume each fitted with a rubber septum. The amounts of gas injected were estimated or calculated as described above for each method of production in order to produce the final concentrations shown in the tables of results. Each treatment was replicated at least twice. Appropriate control insects were also sealed in a similar desiccator to estimate any mortality in untreated insects during the exposure period. After exposing insects to the fumigant for 24, 48 or 72 hours, the desiccators were opened and aired for few minutes; The control and treated insects were transferred to labelled glass tubes containing wheat-feed and kept for one week before estimation of mortality.

Table 1 Insect mortality after various lengths of exposure to 0.2 mg/l methylphosphine gas. Figures are shown mean SEM (n=3)

| INSECT SPECIES | UN- | Percent corrected mortality | | |
|---|---|---|---|---|
| STRAIN | TREATED | 24 | 48 | 72 (Hours) |
| R dominica | | | | |
| Reference | 3.69 ± 2.55 | 0.41 ± 0.58 | 0.00 | 49.010 ± 34 |
| 306-sel | 2.28 ± 85 | 100 | 100 | 100 |
| BR2 | 0.49 ± 0.69 | 96.28 ± 0.97 | 100 | 100 |
| T castaneum | | | | |
| Lab | 0.65 ± 0.91 | 5.99 ± 4.07 | 50.92 ± 9.52 | 100 |
| BT-1vs | 0.00 | 50.10 ± 2.48 | 100 | 100 |
| S Oryzae | | | | |
| Reference | 0.34 ± 0.48 | 0.52 ± 0.74 | 6.52 ± 1.99 | 32.795.54 |
| 476s | 0.93 ± 0.91 | 15.52 ± 9.06 | 79.15 ± 0.35 | 96.19 ± 1.25 |
| C ferruginous | | | | |
| Reference | 2.81 ± 0.83 | 9.31 ± 2.55 | 3.36 ± 0.58 | 31.55 ± 7.05 |
| RR | 4.08 ± 1.13 | 32.28 ± 1.67 | 95.84 ± 0.83 | 97.99 ± 0.67 |

EXPERIMENT 1: Methylphosphine was prepared and its concentration was estimated using Method 1. As shown in Table 1, methylphosphine treatment of all insect species tested produced a much higher mortality in the resistant strains compared to the corresponding susceptible insects.

In the case of R dominica, a 24 hour treatment with 0.2 mg/l of methylphosphine resulted in a much higher mortality in both of the resistant strains (306-sel & BR2) compared to a negligible kill in the susceptible strains whilst no mortality resulted in susceptible insects after 48 hours exposure and half of them still survived after 72 hours exposure (Table 1).

Compared to this, addition of 0.05 mg/l of phosphine gas to different concentrations of methylphosphine apparently killed all the susceptible insects after 24 hours (Table 2).

Table 2—Insect mortality after 24 hour exposure to 0.05 mg/l phosphine plus various concentrations of methylphosphine gas.

| INSECT SPECIES | | Percent corrected mortality | | | |
|---|---|---|---|---|---|
| STRAIN | UNTREATED | 0.05 | 0.10 | 0.20 | (mg/l) |
| R dominica | | | | | |
| Reference | 2.5 | 100 | 100 | 100 | |
| 306-sel | 1.6 | 0 | 84.7 | 100 | |
| BR2 | 2.0 | 0 | 43.2 | 100 | |
| T castaneum | | | | | |
| Lab | 0 | 100 | 100 | 100 | |
| BT-1vs | 0 | 0 | 100 | 100 | |

With T castaneum, a 24 hour exposure to 0.2 mg/l of methylphosphine produced 50% kill in the resistant strain compared to only about 6% mortality in the susceptible insects. A 48 hours exposure to this dose completely killed all the resistant insects whilst about half of the susceptible insects survived (Table 1). The susceptible insects were however completely killed when exposed to 0.2 mg/l of methylphosphine for 72 hours (Table 1) or to a mixture of different concentrations of methylphosphine econtaining 0.05 mg/l of phosphine gas (Table 2).

The strains of S oryzea and C ferrugineus tested also showed a similar trend. The resistant strains of both species suffered much higher mortality than their corresponding susceptible strains after treatment with 0.2 mg/l of methylphosphine for 24, 48 and 72 hours (Table 1).

The few insects that survived the longest treatment period were, however, highly affected and unable to move normally. In common with other species, treatment with a mixture of methylphosphine and 0.05 mg/l of phosphine killed all the susceptible insects from each species (data not included).

EXPERIMENT 2: In order to more precisely quantify the toxicity of the methylphosphine to these insect species, methylphosphine was prepared and accurately assayed by Method 2. The results of the tests are shown in Table 3.

In the case of R dominica, a comparison of LC50 values indicates that almost 4–8 times higher amounts of methylphosphine were needed to kill $PH_3$-susceptible insects compared to the two $PH_3$-resistant strains.

Interestingly, in terms of molarity, the LC99 value for the resistant insects is comparable to the discriminating dose of $PH_3$ required to kill all susceptible insects (Table 4).

Similar effects of methylphosphine on PH3-resistant and susceptible insects of S oryzae were observed. Whilst a 24-hour exposure to 0.0162 mg/l would have killed 50% of the $PH_3$-resistant (476s) strain, a concentration of almost 7 times higher (0.1196 mg/l) was required to kill 50% of susceptible insects. A similar difference in the toxicity of methylphosphine to $PH_3$-resistant and susceptible insects was observed at the LC99.9 level.

Table 3—Toxicity of methylphosphine to adults of phosphine-resistant and susceptible strains of four species of stored-product beetles over a 24-hour exposure at 25° C. (concentrations in mg/l).

| INSECT SPECIES/ STRAIN | LC50 | 95% Fiducial limit | LC99.9 | 95% Fiducial limit | Slope | p-Value |
|---|---|---|---|---|---|---|
| R dominica | | | | | | |
| Susceptible | 0.1016 | | | 0.1365 (90%)* | | 0.0105 |
| 306-sel | 0.0129 | 0.0118–0.0140 | 0.0468 | 0.0389–0.0615 | 5.54 | 0.9705 |
| BR2 | 0.0229 | 0.0218–0.0242 | 0.0473 | 0.0417–0.0561 | 9.83 | 0.4276 |
| T castaneum | | | | | | |
| Susceptible | 0.0113 | 0.0017–0.0167 | 0.0860 | 0.0538–0.8594 | 3.50 | 0.9020 |
| BT-1vs | 0.0168 | 0.0063–0.0215 | 0.0497 | 0.0303–440 | 6.55 | 0.0050 |
| S oryzae | | | | | | |
| Susceptible | 0.1196 | 0.1084–0.1287 | 0.4607 | 0.3734–0.6393 | 5.28 | 0.1048 |
| 476s | 0.0162 | 0.0147–0.0174 | 0.0590 | 0.0469–0.0857 | 5.51 | 0.4805 |
| C ferruginous | | | | | | |
| Susceptible | 0.0747 | | | 0.1165 (99%)* | | 0.8931 |
| BC12s | 0.0338 | 0.0277–0.0405 | 0.1102 | 0.0795–0.2427 | 6.17 | <0.001 |

*Insignificant slope.

The concentration of methylphosphine which produced 99.9% mortality in S oryzae $PH_3$-resistant insects is comparable to the discriminating concentration of $PH_3$ which kills all susceptible insects of the species.

The dose-response line for the PH3-resistant (BT1vs) strain of T castaneum was not statistically significant and the LC50 values indicate that a similar concentration of methylphosphine is required to kill PH3-resistant and $PH_3$- susceptible insects. At the LC99.9 level, however, about a two fold concentration of methylphosphine was required to kill $PH_3$-susceptible insects than then PH3-resistant ones. Also, in common with R dominica and S oryzae, LC99.9 for the BT1vs strain is comparable with the discriminating dose of $PH_3$ which kills all $PH_3$-susceptible insects of this species.

Table 4—Discriminating dose of phosphine for adults of phosphine-resistant and susceptible strains of four species of stored-product beetles over a 20-hour exposure (concentrations in mg/l)

| INSECT | DOSE |
| --- | --- |
| R dominica | 0.03 |
| T castaneum | 0.04 |
| S oryzae | 0.04 |
| C ferrugineus | 0.06 |

All data from "FAO method No 15", FAO Plant Prot Bull 23,12 except C ferrugineus from Mills (1983) Proc of The Second European Congress of Entomology pp. 98–101, Kiel, West Germany.

The $PH_3$-resistant and susceptible strains of C ferrugineus also had a similar response to methylphosphine treatment. At the LC50 level, almost a two-fold higher concentration of methylphosphine was required to kill $PH_3$-susceptible insects compared to $PH_3$-resistant insects. Because of the insignificant slope of the probit line for susceptible insects, a comparison of LC99.9 values was not possible. However, on molar basis, the LC99.9 of methylphosphine for the $PH_3$-resistant (BC12s) strain is quite close to the discriminating dose of $PH_3$ for this species.

CONCLUSIONS: These results clearly demonstrate that methylphosphine has much greater toxic effects on PH3-resistant insects than on susceptible ones. A similar trend in all four insect species tested suggests a ccmmon mechanism of PH3-resistance in insects. It is possible that the presence of an alkyl, and in particular a methyl group, in the alkylphosphine molecule prevents exclusion by the resistance mechanism and the metabolic detoxification process may produce the $PH_3$molecule inside the insect tissues, causing severe insidious toxic effects in resistant insects.

Methylphosphine can therefore be used to selectively control $PH_3$-resistant insects, although higher doses of this gas (or longer exposure periods or a combination of both) can also be utilised to kill both susceptible and resistant insects. The gaseous nature of methylphosphine means that its use as a fumigant alone or in mixture with $PH_3$ is possible.

What is claimed is:

1. A fumigant composition comprising a compound of the formula (i):

wherein said compound constitutes at least 1% of the composition;

wherein R is an optionally substituted $C_1$–$C_6$ aliphatic hydrocarbyl group and R' is H or an optionally substituted $C_1$–$C_6$ aliphatic hydrocarbyl group, wherein the substituents of the hydrocarbyl group are selected from: mercapto; fluoro; chloro; bromo; iodo; cyano;

and at least one additional gas.

2. A composiiton as claimed in claim 1 wheren the additional gas is $CO_2$.

3. A composition as claimed in claim 1 wherein the compound of formula (i) constitutes at least 5% of the composition.

4. A composition as claimed in claim 3 wherein the concentration of the compound of formula (i) in the composition is selected such as to minimize flammability of the composition.

5. A compostion as claimed in claim 1 wherein the additional gas is $PH_3$.

6. A composition as claimed in claim 5 wherein the ratio of the compound of the formula (i): $PH_3$ is around 2:1.

7. A compostion as claimed in claim 5 wherein the ratio of the compound of formula (i): $PH_3$ is selected such that the composition has approximately equivalent pesticidal affect against phosphine resistant and phosphine susceptible pest.

8. A composition as claimed in claim 3 wherein the compound of formula (i) constitutes at least 10% of the composition.

9. A composition as claimed in claim 3 wherein the compound of formula (i) constitutes at least 50% of the composition.

10. A composition as claimed in claim 3 wherein the compound of formula (i) constitutes at least 85% of the composition.

11. A composition as claimed in claim 3 wherein the additional gas is selected such as to minimize flammability of the composition.

12. A composition as claimed in claim 11 wherein both the additional gas and the concentration of the compound of formula (i) in the composition are selected such as to minimize flammability of the composition.

* * * * *

UNITED STATES PATENT AND TRADEMARK OFFICE
CERTIFICATE OF CORRECTION

PATENT NO. : 6,096,330  
DATED : August 1, 2000  
INVENTOR(S) : Mohammad Qasim Chaudhry, Alan Donald Macmicoll, and Nicholas Raymond Price Page 1 of 1

It is certified that error appears in the above-identified patent and that said Letters Patent is hereby corrected as shown below:

Title page, item [75],  
Line 1, cancel "Oasim" and in its place insert -- Qasim --.

Item 73,  
Cancel the words "The Secretary of State for".

Abstract,  
Item [57],  
Line 6, cancel "metliylphosphiine" and in it place insert -- methylphosphine --.

Column 5,  
Line 44, cancel "METMYMPHOSPHINE" and in its place insert -- METHYLPHOSPHINE --.

Column 8,  
Line 7, cancel "EXPEIMENT" and insert in its place -- EXPERIMENT --.

Column 10,  
Line 3, after "formula (i) :" insert the following as a new line: -- (i) R-PH-R' --.

Column 10, claim 7,  
Line 30, cancel "pest" and in its place insert -- pests --.

Signed and Sealed this

Thirtieth Day of October, 2001

*Attest:*

NICHOLAS P. GODICI  
*Attesting Officer*  Acting Director of the United States Patent and Trademark Office